United States Patent
Alig et al.

(10) Patent No.: US 6,423,859 B1
(45) Date of Patent: Jul. 23, 2002

(54) PROCESS FOR THE PREPARATION OF ORGANOSILYLALKYLPOLYSULFANES

(75) Inventors: Alfred Alig, Geiselbach-Omersbach; Christoph Batz-Sohn, Hanau-Mittelbuchen; Ulrich Deschler, Sailauf; Rudolf Michel, Freigericht; Jörg Münzenberg, Hanau, all of (DE); Raymund Sonnenschein, Mobile, AL (US); Werner Will, Gelnhausen (DE); Gerd Rainhard Zezulka, Hanau (DE); Karl-Heinz Rützel, Hürth (DE)

(73) Assignee: Degussa AG, Hanau (DE)

( * ) Notice: Subject to any disclaimer, the term of this patent is extended or adjusted under 35 U.S.C. 154(b) by 0 days.

(21) Appl. No.: 09/903,858

(22) Filed: Jul. 13, 2001

(30) Foreign Application Priority Data

Jul. 15, 2000 (DE) .......................... 100 34 493

(51) Int. Cl.$^7$ ................................................. C07R 7/08
(52) U.S. Cl. ....................................................... 556/427
(58) Field of Search ......................... 556/477

(56) References Cited

U.S. PATENT DOCUMENTS

| | | | | |
|---|---|---|---|---|
| 5,965,760 A | * | 10/1999 | Michel et al. | 556/427 |
| 6,114,560 A | * | 9/2000 | Ichinohe et al. | 556/427 |
| 6,194,595 B1 | * | 2/2001 | Michel et al. | 556/427 |
| 6,274,755 B1 | * | 8/2001 | Munzenberg et al. | 556/427 |

* cited by examiner

*Primary Examiner*—Paul F. Shaver
(74) *Attorney, Agent, or Firm*—Pillsbury Winthrop LLP

(57) ABSTRACT

The invention relates to a process for the preparation of organosilylalkylpolysulfanes, of the general formula I $(R^1R^2R^3SiR^4)_2S_x$ (I) by reaction of organosilylalkylpolysulfanes of the general formula II $(R^1R^2R^3SiR^4)_2S_y$ (II) with an ionic sulfide of the general formula $M^+{}_2S^{2-}$ (III) and an organosilylalkyl halide of the general formula $R^1R^2R^3SiR^4X$ (IV), the long-chain organosilylalkylpolysulfane of the general formula (II) and the organosilylalkyl halide of the general formula (IV) being initially introduced into the reaction vessel and the ionic sulfide of the general formula (III) being added to this solution in several portions.

3 Claims, No Drawings

PROCESS FOR THE PREPARATION OF ORGANOSILYLALKYLPOLYSULFANES

CROSS REFERENCE TO RELATED APPLICATIONS

The present application claims priority under 35 U.S.C § 119 to German application 100 34 493.3, filed on Jul. 15, 2000.

The invention relates to a process for the preparation of organosilylalkylpolysulfanes.

It is known that organosilylalkylpolysulfanes, such as bis(3,3'-triethoxysilylpropyl)tetrasulfane (DE 2 141 159) and -disulfane, are employed as a silane adhesion promoter or reinforcing additive in rubber mixtures comprising oxidic fillers. The rubber mixtures are used, inter alia, for industrial rubber articles and for components of car tyres, in particular for treads (DE 2 141 159, DE 2 212 239, U.S. Pat. No. 3,978,103, U.S. Pat. No. 4,048,206, EP 819694).

It is furthermore known that the alkoxysilyl function, usually a trimethoxysilyl or triethoxysilyl group, reacts with the silanol groups of the filler, usually silicas, during preparation of the mixture and the silane is fixed on the filler surface in this way. The filler-rubber bond is then formed during the vulcanization process via the sulfur functionality of the fixed silane. The reactivity of the organosilylalkylpolysulfanes here depends decisively on the length of the polysulfane chain. Long chains with many sulfur atoms show a high reactivity. However, this high reactivity can lead to an undesirable premature reaction during processing. On the other hand, short-chain derivatives are significantly less reactive, but can be activated in a controlled manner via addition of additional elemental sulfur at a later point in time in the production process. This capacity for controlled activation of the compounds leads to a more economical production of rubber articles and to greater processing reliability. Organosilylalklyldisulfanes with a high disulfane content have particular advantages (EP 732362, L. Panzer, American Chem. Soc., Rubber Div. Meeting 1997).

It is furthermore known that organosilylalkylpolysulfanes with a reduced polysulfane chain length are prepared from the corresponding long-chain organosilylalkylpolysulfanes. EP 0773224 discloses a process in which organosilylalkylpolysulfanes are broken down to the corresponding disulfanes with the aid of cyanides, phosphanes or sulfites. In EP 0845472 and WO 97/48264, organophosphorus(III) compounds (inter alia phosphites and P—N compounds) are used to reduce the polysulfane chains.

These processes have the disadvantage that for each molar equivalent of sulfur removed from the organosilylalkylpolysulfane, one molar equivalent of thiocyanate, organophosphorus(V) sulfide or thiosulfate is formed as a by-product.

EP 0894803 discloses a process in which the thiocyanate formed in the desulfurization with cyanide is reacted with an organosilylalkyl halide to give an organosilylalkyl thiocyanate, which is also reactive in the rubber.

A disadvantage of this process is that a mixture of an organosilylalkyldisulfane and an organosilylalkyl thiocyanate is obtained.

EP 0908463 and EP 0937732 furthermore disclose processes for reducing the sulfur chain length in organosilylalkylpolysulfanes in which the polysulfanes mentioned are reacted with an anhydrous or almost anhydrous ionic sulfide and then with organosilylalkyl halides.

A disadvantage of this process is the formation of considerable amounts of the by-product organosilylalkylmonosulfane, which cannot react with the rubber matrix. Products from this process are thus distinguished by a low content of active compound.

The object of the invention is to provide an alternative process for the preparation of organosilylalkylpolysulfane in which the amount of by-products which have to be disposed of is low.

The invention provides a process for the preparation of organosilylalkylpolysulfanes of the general formula I $$(R^1R^2R^3SiR^4)_2S_x \qquad (I)$$

in which the symbols denote $R^1$, $R^2$, $R^3$: which are identical or different from one another, branched and unbranched alkyl and/or alkoxy groups having a chain length of 1–8 C atoms, preferably 1–3 C atoms, aryl radicals, in particular phenyl, toluyl, benzyl, at least one alkoxy group being present;

$R^4$ divalent alkylene radical having a chain length of 1–8 C atoms, such as, for example, methylene, ethylene, i-propylene, preferably n-propylene, i-butylene, 2-methylpropylene, n-butylene, n-pentylene, 2-methylbutylene, 3-methylbutylene, n-pentylene, 1,3-dimethylpropylene or 2,3-dimethylpropylene, preferably 1 to 4 C atoms, or —(CH$_2$)$_n$—C$_6$H$_4$—(CH$_2$)$_n$— where n=1–4, x: number $\geq 1$, preferably between 2 and 3, which is characterized in that organosilylalkylpolysulfane of the general formula II $$(R^1R^2R^3SiR^4)_2S_y \qquad (II)$$

in which $R^1$, $R^2$, $R^3$ and $R^4$ have the abovementioned meaning and y: number >x, preferably between 2 and 6, particularly preferably between 3 and 5, is reacted with an ionic sulfide of the general formula III $$M^+_2S^{2-} \qquad (III),$$

in which M$^+$ represents an alkali metal cation, for example sodium or potassium cation, an ammonium ion, half an alkaline earth metal cation or half a zinc cation, and an organosilylalkyl halide of the general formula IV $$R^1R^2R^3SiR^4X \qquad (IV)$$

in which $R^1$, $R^2$, $R^3$ and $R^4$ have the abovementioned meaning and

X: is chlorine bromine or iodine, the long-chain organosilylalkylpolysulfane of the general formula (II) and the organosilylalkyl halide of the general formula (IV) being initially introduced into the reaction vessel and the ionic sulfide of the general formula (III) being added to this solution in several portions.

Because of the susceptibility of the starting substances according to formula (II) and formula (IV) to hydrolysis, the sulfides of the general formula III can be anhydrous or almost anhydrous. The sulfide of the general formula III can contain a maximum of 10 wt. %, preferably 0–5 wt. %, particularly preferably 0–2 wt. % of water. Sulfides of the general formula III can be obtained by:

1. Reaction of alkali metal alcoholates with hydrogen sulfide (EP 705838).

2. Reaction of ammonia gas with hydrogen sulfide (DE 2648241).
3. Drying of alkali metal sulfide hydrates (JP 7228588, DE 19610281, DE 19651849).

It is irrelevant here whether the drying of the alkali metal sulfide hydrates is carried out azeotropically or by heating in vacuo. The ionic sulfide required can advantageously be prepared by the process described in DE 196 51849.

The ionic sulfide of the general formula (III) can be employed in the form of a solid, either as a ground powder or as platelets, such as are available in the case of commercially obtainable alkali metal sulfide hydrates, or in the form of a solution or suspension of the solid in an organic solvent.

All polar solvents in which the ionic sulfide of the general formula (III) is at least partly soluble and which do not react with the organosilicon compound of the general formula (II) can be employed as the polar organic solvent.

The molar ratios of the educts according to formulae (II) and (III) can depend on what average polysulfane chain length y is present in the starting compound and what average polysulfane chain length x is to be obtained in the end product.

The molar ratio between the ionic sulfide of the formula (III) and the organosilylalkyl halide of the formula (IV) can in turn depend on the active compound content of the ionic sulfide. It can be between 1.5 and 2.5 molar equivalents, preferably between 1.8 and 2.2 molar equivalents of organosilylalkyl halide of the formula (IV) per molar equivalent of ionic sulfide of the formula (III).

The reaction can be carried out with exclusion of air and water (moisture), in order to suppress or avoid to the greatest extent the formation of by-products. The reaction can be carried out at elevated temperature. It is not essential here for the process according to the invention whether, to achieve the reaction temperature, the reaction mixture must be heated externally or heats up by itself due to the exothermicity released. The reaction can be carried out at between room temperature and 200° C., preferably between 40° C. and the boiling temperature of the solvent employed. The reaction can be carried out under normal pressure, reduced or elevated pressure.

After the reaction, the ionic halide which has precipitated out can be filtered off and the solvent can be distilled off.

By this procedure, the organosilylalkylpolysulfanes of the formula (I) can be prepared without the troublesome formation of unreactive by-products which cannot be separated off.

The polysulfane chain lengths x in the formula (I) and y in the formula (II) are to be understood as mean values. The values x and y designate the average lengths of the polysulfane unit present in the product mixture.

Since the polysulfane chain length of the compound of the formula (II) is to be reduced in the reaction according to the invention, so that the compound of the formula (I) results, y must be >x.

In a particularly preferred embodiment of the invention, the organosilylalkylpolysulfane of the general formula (II) can already be reacted with the ionic sulfide of the general formula (III) and the organosilylalkyl halide of the general formula (IV) during its formation (in situ). In this case the organosilylalkylpolysulfane of the general formula (II) prepared in situ from an organosilylalkyl halide of the general formula IV and an ionic polysulfide of the general formula V $$M^+{}_2 S_y{}^{2-}$$ (V)

in which $M^+$ and y have the abovementioned meaning, can be reacted with an ionic sulfide of the general formula (III) and further organosilylalkyl halide of the general formula (IV). The reaction can be carried out in a polar organic solvent. The organosilylalkyl halide of the general formula (IV) necessary for the reaction can be heated with the ionic polysulfide of the general formula (V) and the ionic sulfide of the general formula (III) necessary for reducing the polysulfane chain length can be metered in at elevated temperature in several portions.

The content of sulfur in the ionic polysulfide of the general formula (V) can be identical to the average polysulfane chain length y of the organosilicon polysulfide of the formula (II) which can be formed intermediately. Ionic polysulfides of the general formula (V) which can be used are, preferably, sodium, potassium or ammonium polysulfide, particularly preferably sodium polysulfide. Because of the susceptibility of the starting substances according to formula (II) and formula (IV) to hydrolysis, the ionic polysulfides of the general formula (V) can be anhydrous or almost anhydrous. The polysulfide of the general formula (V) can contain a maximum of 10 wt. % of water, preferably 0–5 wt. %, particularly preferably 0–2 wt. %. Polysulfides of the general formula (V) can be obtained by:
1. Reaction between an anhydrous or almost anhydrous sulfide and sulfur (JP 7228588)
2. Reaction between elemental alkali metals and sulfur, either in the melt (U.S. Pat. No. 4,640,832) or in an inert solvent (DE 19819373, EP 949263, G. Brauer, Handbuch der praparativen anorganischen Chemie [Handbook of Preparative Inorganic Chemistry], 3 rd edition, Stuttgart 1975, volume 1, p. 376 ff)
3. Reaction between alcoholates and sulfur (U.S. Pat. No. 5,596,116)
4. Reaction between water-containing alkali metal sulfide and sulfur with subsequent drying (DE 19651849)
5. Reaction between alkali metal hydroxide and sulfur with subsequent drying (DE 19930495)

The ionic polysulfide according to formula (V) can be employed in the form of a solid (powder, granules) or in the form of a solution or suspension of the solid in an organic solvent, without affecting the success of the reaction.

In the particularly preferred embodiment of the invention, in which the organosilylalkylpolysulfane of the formula (II) is already reacted further to give the target compound of the formula (I) during its formation, the molar ratio between the ionic polysulfide of the formula (V) used for the preparation of the organosilylalkylpolysulfane of the formula (I) and the ionic sulfide according to formula (III) can be established such that the average sulfur content of this mixture approximately corresponds to the average sulfur chain length x in the target compound (I). The molar ratio between the ionic polysulfide of the formula (V) and the ionic sulfide of the formula (III) and the organosilylalkyl halide of the formula (IV) can in turn depend on the active compound content of the ionic polysulfide and sulfide. It can be between 1.5 and 2.5 molar equivalents, preferably between 1.8 and 2.2 molar equivalents of organosilylalkyl halide of the formula (IV) per molar equivalent of polysulfide and sulfide.

EXAMPLES

Comparison Example 1

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide 67.4 g (0.13 mol) bis(3,3'-triethoxysilylpropyl) tetrasulfane and 18.5 g (0.24 mol) sodium sulfide in 120 ml ethanol are initially introduced into a 500 ml three-necked flask with a reflux condenser and magnetic stirrer under $N_2$ inert gas. 108.7 g (0.45 mol) 3-chloropropyltriethoxysilane are added at room temperature and the reaction mixture is kept at the reflux temperature for 2.5 h. After cooling to room temperature, the precipitate is filtered off and the residue on the filter is washed 3 times with 30 ml ethanol each time. The collected filtrates are concentrated in a rotary evaporator at 110° C. down to a final vacuum of 40 mbar. This gives 153.1 g of a yellow liquid which, according to analysis by $^1$H-NMR spectroscopy, corresponds to a polysulfane mixture with an average polysulfane chain length of 2.0. The product contains 10 wt. % monosulfane ($\delta$ 2.5 ppm). Yield: 90°% (based on 3-chloropropyltriethoxysilane).

Example 1

Preparation of Bis(3,3'-Triethoxysilylpropyl) disulfane from bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol) 3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in four equal portions with a time interval of 5 min in each case. During this procedure the reaction mixture heats up further to the boiling temperature. After the last addition of sodium sulfide the mixture is heated under reflux for a further 2 h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 152.3 g of a yellow liquid which, according to analysis by $^1$H-NMR spectroscopy, corresponds to a polysulfane mixture with an average polysulfane chain length of 2.0. The product contains 2.1° wt. % monosulfane ($\delta$° 2.5 ppm). Yield: 91% (based on 3-chloropropyltriethoxysilane).

Example 2

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol) 3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in four equal portions with a time interval of 10 min in each case. During this procedure the reaction mixture heats up further to the boiling temperature. After the last addition of sodium sulfide the mixture is heated under reflux for a further 2 h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 150.7 g of a yellow liquid which, according to analysis by $^1$H-NMR spectroscopy, corresponds to a polysulfane mixture with an average polysulfane chain length of 2.0. The product contains 2 wt. % monosulfane ($\delta$° 2.5 ppm). Yield: 88°% (based on 3-chloropropyltriethoxysilane).

Example 3

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol) 3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in four equal portions with a time interval of 15 min in each case. During this procedure the reaction mixture heats up further to the boiling temperature. After the last addition of sodium sulfide the mixture is heated under reflux for a further 2 h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 152.4 g of a yellow liquid which, according to analysis by $^1$H-NMR spectroscopy, corresponds to a polysulfane mixture with an average polysulfane chain length of 2.0. The product contains 1.9 wt. % monosulfane ($\delta$ 2.5 ppm). Yield: 91% (based on 3-chloropropyltriethoxysilane).

Example 4

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol) 3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in five equal portions with a time interval of 5 min in each case. During this procedure the reaction mixture heats up further to the boiling temperature. After the last addition of sodium sulfide the mixture is heated under reflux for a further 2° h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 149.1 g of a yellow liquid which, according to analysis by $^1$H-NMR spectroscopy, corresponds to a polysulfane mixture with an average polysulfane chain length of 2.0. The product contains 2.0° wt. % monosulfane ($\delta$ 2.5° ppm). Yield: 89% (based on 3-chloropropyltriethoxysilane).

Example 5

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol)

3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in five equal portions with a time interval of 10 min in each case. During this procedure the reaction mixture heats up further to the boiling temperature. After the last addition of sodium sulfide the mixture is heated under reflux for a further 2 h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 154.1 g of a yellow liquid which, according to analysis by $^1$H-NMR spectroscopy, corresponds to a polysulfane mixture with an average polysulfane chain length of 2.0. The product contains 1.8 wt. % monosulfane (δ 2.5° ppm). Yield: 92% (based on 3-chloropropyltriethoxysilane).

Example 6

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol) 3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in ten equal portions with a time interval of 5 min in each case. During this procedure the reaction mixture heats up further to the boiling temperature. After the last addition of sodium sulfide the mixture is heated under reflux for a further 2° h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 149.0 g of a yellow liquid which, according to analysis by $^1$H-NMR spectroscopy, corresponds to a polysulfane mixture with an average polysulfane chain length of 2.0. The product contains 1.6° wt. % monosulfane (δ 2.5° ppm). Yield: 89% (based on 3-chloropropyltriethoxysilane).

Example 7

Preparation of Bis(3,3'-Triethoxysilylpropyl) disulfane from Bis(3,3'-Triethoxysilylpropyl) tetrasulfane, 3-Chloropropyltriethoxysilane and Sodium Sulfide with Metering in of the Sodium Sulfide in Portions 67.4 g (0.13 mol) bis(3,3'-triethoxysilylpropyl) tetrasulfane and 108.7 g (0.45 mol) 3-chloropropyltriethoxysilane in 120 ml ethanol are initially introduced into a 500 ml three-necked flask with a reflux condenser and magnetic stirrer under $N_2$ inert gas and heated to 60° C. A total of 18.5 g (0.24 mol) sodium sulfide is added to this reaction mixture in ten equal portions with a time interval of 10 min in each case. During this procedure the reaction mixture heats up further to the boiling temperature. After the last addition of sodium sulfide the mixture is heated under reflux for a further 2 h. After cooling to room temperature, the precipitate is filtered off and the residue on the filter is washed 3 times with 30 ml ethanol each time. The collected filtrates are concentrated in a rotary evaporator at 110° C. down to a final vacuum of 40° mbar. This gives 150.7 g of a yellow liquid which, according to analysis by $^1$H-NMR spectroscopy, corresponds to a polysulfane mixture with an average polysulfane chain length of 2.0. The product contains 1.7 wt. % monosulfane (δ° 2.5° ppm). Yield: 90% (based on 3-chloropropyltriethoxysilane).

Comparison Example 2

Preparation of Bis(3,3'-Triethoxysilylpropyl) disulfane from 3-Chloropropyltriethoxysilane, Sodium Tetrasulfide and Sodium Sulfide 21.8 g (0.13 mol) sodium tetrasulfide, 19.5 g sodium sulfide (0.25 mol) and 180.6 g (0.75 mol) 3-chloropropyltriethoxysilane are heated together to 50° C. in 180 ml ethanol in a 500 ml three-necked flask with a reflux condenser and magnetic stirrer under $N_2$ inert gas. At this temperature an exothermicity is observed which brings the reaction mixture to the boiling temperature. The reaction mixture is kept at the boiling temperature for 2.5 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 171.4 g of a yellow liquid which, according to analysis by $^1$H-NMR spectroscopy, corresponds to a polysulfane mixture with an average polysulfane chain length of 2.0. The mixture contains 39° wt. % monosulfane (δ 2.5 ppm). Yield 96% (based on 3-chloropropyltriethoxysilane).

Example 8

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in two equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 164.5 g of a yellow liquid which, according to analysis by $^1$H-NMR spectroscopy, corresponds to a polysulfane mixture with an average polysulfane chain length of 2.1. The mixture contains 7.0 wt. % monosulfane (δ 2.5 ppm). Yield 92% (based on 3-chloropropyltriethoxysilane).

Example 9

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in two equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 158.9 g of a yellow liquid which, according to analysis by $^1$H-NMR spectroscopy, corresponds to a polysulfane mixture with an average polysulfane chain length of 2.1. The mixture contains 6.5 wt. % monosulfane ($\delta°$ 2.5 ppm). Yield 89% (based on 3-chloropropyltriethoxysilane).

Example 10

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in two portions at an interval of 10 min in each case, the first portion being twice the amount of the second. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 161.2 g of a yellow liquid which, according to analysis by $^1$H-NMR spectroscopy, corresponds to a polysulfane mixture with an average polysulfane chain length of 2.0. The mixture contains 7.5° wt. % monosulfane ($\delta$ 2.5 ppm). Yield 91% (based on 3-chloropropyltriethoxysilane).

Example 11

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in four equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 159.8 g of a yellow liquid which, according to analysis by $^1$H-NMR spectroscopy, corresponds to a polysulfane mixture with an average polysulfane chain length of 2.0. The mixture contains 3.6 wt. % monosulfane ($\delta°$ 2.5 ppm). Yield 90% (based on 3-chloropropyltriethoxysilane).

Example 12

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in four equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 163.2 g of a yellow liquid which, according to analysis by $^1$H-NMR spectroscopy, corresponds to a polysulfane mixture with an average polysulfane chain length of 2.0. The mixture contains 3.3 wt. % monosulfane ($\delta°$ 2.5 ppm). Yield 92% (based on 3-chloropropyltriethoxysilane).

Example 13

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in four portions at an interval of 10 min in each case, the first and second portion being twice the amount of the others. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 159.6 g of a yellow liquid which, according to analysis by $^1$H-NMR spectroscopy, corresponds to a polysulfane mixture with an average polysulfane chain length of 2.0. The mixture contains 4.1 wt. % monosulfane ($\delta°$ 2.5 ppm). Yield 90% (based on 3-chloropropyltriethoxysilane).

Example 14

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol. are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in four portions at an interval of 10 min in each case, the last two portions being twice the amount of the first ones. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 161.4 g of a yellow liquid which, according to analysis by $^1$H-NMR spectroscopy, corresponds to a polysulfane mixture with an average polysulfane chain length of 2.0. The mixture contains 4.3 wt. % monosulfane ($\delta$° 2.5 ppm). Yield 91% (based on 3-chloropropyltriethoxysilane).

Example 15

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in five equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 160.7 g of a yellow liquid which, according to analysis by $^1$H-NMR spectroscopy, corresponds to a polysulfane mixture with an average polysulfane chain length of 2.1. The mixture contains 3.3 wt. % monosulfane ($\delta$° 2.5 ppm). Yield 90% (based on 3-chloropropyltriethoxysilane).

Example 16

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in five equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 157.7 g of a yellow liquid which, according to analysis by $^1$H-NMR spectroscopy, corresponds to a polysulfane mixture with an average polysulfane chain length of 2.0. The mixture contains 3.2 wt. % monosulfane ($\delta$° 2.5 ppm). Yield 89% (based on 3-chloropropyltriethoxysilane).

Example 17

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in five portions at an interval of 10 min in each case, the first three portions comprising 80% of the total amount metered in. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 163.4 g of a yellow liquid which, according to analysis by $^1$H-NMR spectroscopy, corresponds to a polysulfane mixture with an average polysulfane chain length of 2.0. The mixture contains 3.4 wt. % monosulfane ($\delta$ 2.5 ppm). Yield 92% (based on 3-chloropropyltriethoxysilane).

Example 18

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in ten equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 163.0 g of a yellow liquid which, according to analysis by $^1$H-NMR spectroscopy, corresponds to a polysulfane mixture with an average polysulfane chain length of 2.0. The mixture contains 2.8 wt. % monosulfane ($\delta$° 2.5 ppm). Yield 92% (based on 3-chloropropyltriethoxysilane).

Example 19

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in ten equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 162.7 g of a yellow liquid which, according to analysis by $^1$H-NMR spectroscopy, corresponds to a polysulfane mixture with an average polysulfane chain length of 2.1. The mixture contains 2.9 wt. % monosulfane (δ 2.5 ppm). Yield 91% (based on 3-chloropropyltriethoxysilane).

Example 20

Preparation of Bis(3,3'-Triethoxysilylpropyl) disulfane from 3-Chloropropyltriethoxysilane, Sodium Tetrasulfide and Sodium Sulfide with Metering in of the Sodium Sulfide in Portions 21.8 g (0.13 mol) sodium tetrasulfide and 180.6 g (0.78° mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 21.5 g (0.27 mol) sodium sulfide is added to the reaction mixture in ten portions at an interval of 10 min in each case, the first five portions comprising 66% of the total amount. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40° mbar. This gives 161.1 g of a yellow liquid which, according to analysis by $^1$H-NMR spectroscopy, corresponds to a polysulfane mixture with an average polysulfane chain length of 2.1. The mixture contains 3.1 wt. % monosulfane (δ° 2.5 ppm). Yield 90% (based on 3-chloropropyltriethoxysilane).

Comparison Example 3

Preparation of Bis(3,3'-Triethoxysilylpropyl) disulfane from 3-Chloropropyltriethoxysilane, Sodium Tetrasulfide and Sodium Sulfide 21.8 g (0.13 mol) sodium tetrasulfide and 19.5 g sodium sulfide (0.25 mol)in 180 ml ethanol are initially introduced, with stirring, into a 500 ml three-necked flask with a reflux condenser, dropping funnel and magnetic stirrer under $N_2$ inert gas and initially heated to 50° C. 180.6 g (0.75 mol) 3-chloropropyltriethoxysilane are added dropwise at this temperature in the course of 20 min. During this procedure the temperature of the reaction mixture rises to the boiling temperature. The reaction mixture is kept at the boiling temperature for 2.5 h and then cooled to room temperature. The precipitate formed is filtered off and the residue on the filter is washed 3 times with 30 ml ethanol. The collected filtrates are concentrated in a rotary evaporator at 110° C. down to a final vacuum of 40 mbar. This gives 170.2 g of a yellow liquid which, according to analysis by $^1$H-NMR spectroscopy, corresponds to a polysulfane mixture with an average polysulfane chain length of 2.1. The mixture contains 27° wt. % monosulfane (δ 2.5 ppm). Yield 95% (based on 3-chloropropyltriethoxysilane).

Example 21

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in two equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 114.6 g of a yellow liquid which, according to analysis by $^1$H-NMR spectroscopy, corresponds to a polysulfane mixture with an average polysulfane chain length of 2.0. The mixture contains 5.5 wt. % monosulfane (δ 2.5 ppm). Yield 96% (based on 3-chloropropyltriethoxysilane).

Example 22

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in two equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter-is washed 3 times with 30 ml ethanol each time. The collected filtrates are concentrated in a rotary evaporator at 110° C. down to a final vacuum of 40 mbar. This gives 117.8 g of a yellow liquid which, according to analysis by $^1$H-NMR spectroscopy, corresponds to a polysulfane mixture with an average polysulfane chain length of 2.1. The mixture contains 5.1 wt. % monosulfane (δ° 2.5 ppm). Yield 98% (based on 3-chloropropyltriethoxysilane).

Example 23

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in four equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 116.7 g of a yellow liquid which, according to analysis by $^1$H-NMR spectroscopy, corresponds to a polysulfane mixture with an average polysulfane chain length of 2.1. The mixture contains 2.1 wt. % monosulfane ($\delta°$ 2.5 ppm). Yield 97% (based on 3-chloropropyltriethoxysilane).

Example 24

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in four equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 118.9 g of a yellow liquid which, according to analysis by $^1$H-NMR spectroscopy, corresponds to a polysulfane mixture with an average polysulfane chain length of 2.1. The mixture contains 1.9° wt. % monosulfane ($\delta$ 2.5 ppm). Yield 99% (based on 3-chloropropyltriethoxysilane).

Example 25

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in four portions at an interval of 10 min in each case, the first two portions being twice the amount of the remaining ones. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 115.8 g of a yellow liquid which, according to analysis by $^1$H-NMR spectroscopy, corresponds to a polysulfane mixture with an average polysulfane chain length of 2.0. The mixture contains 2.2 wt. % monosulfane ($\delta°$ 2.5 ppm). Yield 98% (based on 3-chloropropyltriethoxysilane).

Example 26

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in four portions at an interval of 10 min in each case, the last two meterings being twice the amount of the first ones. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 114.3 g of a yellow liquid which, according to analysis by $^1$H-NMR spectroscopy, corresponds to a polysulfane mixture with an average polysulfane chain length of 2.1. The mixture contains 2.4 wt. % monosulfane ($\delta°$ 2.5 ppm). Yield 95% (based on 3-chloropropyltriethoxysilane).

Example 27

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in five equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 115.4 g of a yellow liquid which, according to analysis by $^1$H-NMR spectroscopy, corresponds to a polysulfane mixture with an average polysulfane chain length of 2.1. The mixture contains 1.9 wt. % monosulfane ($\delta°$ 2.5 ppm). Yield 96% (based on 3-chloropropyltriethoxysilane).

Example 28

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in five equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 116.0 g of a yellow liquid which, according to analysis by $^1$H-NMR spectroscopy, corresponds to a polysulfane mixture with an average polysulfane chain length of 2.0. The mixture contains 1.6 wt. % monosulfane ($\delta°$ 2.5 ppm). Yield 98% (based on 3-chloropropyltriethoxysilane).

Example 29

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in five portions at an interval of 10 min in each case, the first two meterings comprising 60% of the total amount. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 116.0 g of a yellow liquid which, according to analysis by $^1$H-NMR spectroscopy, corresponds to a polysulfane mixture with an average polysulfane chain length of 2.0. The mixture contains 2.0 wt. % monosulfane ($\delta°$ 2.5 ppm). Yield 97% (based on 3-chloropropyltriethoxysilane).

Example 30

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in five portions at an interval of 10 min in each case, the last two meterings comprising 60% of the total amount metered in. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 117.6 g of a yellow liquid which, according to analysis by $^1$H-NMR spectroscopy, corresponds to a polysulfane mixture with an average polysulfane chain length of 2.1. The mixture contains 2.2° wt. % monosulfane ($\delta$ 2.5 ppm). Yield 98% (based on 3-chloropropyltriethoxysilane).

Example 31

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in ten equal portions at an interval of 5 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 112.1 g of a yellow liquid which, according to analysis by $^1$H-NMR spectroscopy, corresponds to a polysulfane mixture with an average polysulfane chain length of 2.0. The mixture contains 1.7 wt. % monosulfane ($\delta°$ 2.5 ppm). Yield 94% (based on 3-chloropropyltriethoxysilane).

Example 32

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in ten equal portions at an interval of 10 min in each case. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 111.2 g of a yellow liquid which, according to analysis by $^1$H-NMR spectroscopy, corresponds to a polysulfane mixture with an average polysulfane chain length of 2.0. The mixture contains 1.4 wt. % monosulfane ($\delta°$ 2.5 ppm). Yield 93% (based on 3-chloropropyltriethoxysilane).

Example 33

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in ten portions at an interval of 10 min in each case, the first five meterings comprising in total 66% of the total amount. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 112.5 g of a yellow liquid which, according to analysis by $^1$H-NMR spectroscopy, corresponds to a polysulfane mixture with an average polysulfane chain length of 2.0. The mixture contains 1.6 wt. % monosulfane ($\delta°$ 2.5 ppm). Yield 94% (based on 3-chloropropyltriethoxysilane).

Example 34

Preparation of Bis(3,3'-Triethoxysilylpropyl) disulfane from 3-Chloropropyltriethoxysilane, Sodium Trisulfide and Sodium Sulfide with Metering in of the Sodium Sulfide in Portions 17.8 g (0.13 mol) sodium trisulfide and 120.4 g (0.5 mol) 3-chloropropyltriethoxysilane in 190 ml ethanol are heated to 50° C. in a 500 ml three-necked flask with a reflux condenser and magnetic stirrer under $N_2$ inert gas. An exothermicity is noticed at this temperature. A total of 9.8 g (0.13 mol) sodium sulfide is added to the reaction mixture in ten portions at an interval of 10 min in each case, the last five meterings comprising in total 66% of the total amount. Heating of the reaction mixture is again noticed at each addition of sodium sulfide. After the last addition of sodium sulfide, the reaction mixture is kept at the boiling temperature for a further 2 h and then cooled to room temperature. The precipitate formed is filtered off and the residue on the filter is washed 3 times with 30 ml ethanol each time. The collected filtrates are concentrated in a rotary evaporator at 110° C. down to a final vacuum of 40 mbar. This gives 114.3 g of a yellow liquid which, according to analysis by $^1$H-NMR spectroscopy, corresponds to a polysulfane mixture with an average polysulfane chain length of 2.1. The mixture contains 1.8 wt. % monosulfane ($\delta°$ 2.5 ppm). Yield 95% (based on 3-chloropropyltriethoxysilane).

What is claimed is:

1. Process for the preparation of organosilylalkylpolysulfanes of the general formula $$(R^1R^2R^3SiR^4)_2S_x \qquad (I)$$

in which the symbols denote $R^1$, $R^2$, $R^3$: which are identical or different from one another, branched and unbranched alkyl and/or alkoxy groups having a chain length of 1–8 C atoms, aryl radicals, at least one alkoxy group being present, $R^4$ divalent alkylene radical having a chain length of 1–8 C atoms, or —$(CH_2)_n$—$C_6H_4$—$(CH_2)_n$— where n=1–4, x: number $\geq 1$, characterized in that organosilylalkylpolysulfanes of the general formula II $$(R^1R^2R^3SiR^4)_2S_y \qquad (II)$$

in which $R^1$, $R^2$, $R^3$ and $R^4$ have the abovementioned meaning and y number >x, are reacted with an ionic sulfide of the general formula (III)

$$M^+_2S^{2-} \qquad (III)$$

in which $M^+$ represents an alkali metal cation, an ammonium ion, half an alkaline earth metal cation or half a zinc cation, and an organosilylalkyl halide of the general formula $$R^1R^2R^3SiR^4X \qquad (IV)$$

in which $R^1$, $R^2$, $R^3$ and $R^4$ have the abovementioned meaning and X: is chlorine, bromine or iodine, the long-chain organosilylalkylpolysulfane of the general formula (II) and the organosilylalkyl halide of the general formula (IV) being initially introduced into the reaction vessel and the ionic sulfide of the general formula (III) being added to this solution in several portions.

2. Process for the preparation of organosilylalkylpolysulfanes according to claim 1, characterized in that the reaction is carried out at between RT and 200° C.

3. Process for the preparation of organosilylalkylpolysulfanes according to claim 1, characterized in that the organosilylalkylpolysulfane of the general formula II is already reacted with the ionic sulfide of the general formula III and the organosilylalkyl halide of the general formula IV in situ during its formation from an organosilylalkyl halide of the general formula IV and an ionic polysulfide of the general formula V $$M^+_2S_y^{2-} \qquad (V)$$

in which $M^+$ and y have the abovementioned meaning.

* * * * *